United States Patent
Boese et al.

(10) Patent No.: US 7,354,196 B2
(45) Date of Patent: Apr. 8, 2008

(54) DEVICE FOR RECORDING PROJECTION IMAGES

(75) Inventors: Jan Boese, Eckental (DE); Martin Kleen, Furth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/390,734

(22) Filed: Mar. 28, 2006

(65) Prior Publication Data

US 2006/0222148 A1    Oct. 5, 2006

(30) Foreign Application Priority Data

Mar. 29, 2005   (DE)   ................. 10 2005 014 188

(51) Int. Cl.
*G21K 4/00*   (2006.01)
(52) U.S. Cl. ..................... 378/190; 378/189
(58) Field of Classification Search .............. 378/4, 378/11, 189, 193–198, 205, 19, 190, 204
See application file for complete search history.

(56) References Cited

U.S. PATENT DOCUMENTS

| | | | | |
|---|---|---|---|---|
| 4,501,011 A | * | 2/1985 | Hauck et al. ................ | 378/196 |
| 5,050,204 A | * | 9/1991 | Siczek et al. ................ | 378/197 |
| 5,319,205 A | * | 6/1994 | Kline et al. ............. | 250/363.04 |
| 5,410,584 A | * | 4/1995 | Schaefer et al. ............. | 378/196 |
| 5,485,502 A | * | 1/1996 | Hinton et al. ................ | 378/117 |
| 5,486,700 A | * | 1/1996 | Silberklang et al. ... | 250/363.04 |
| 5,515,416 A | * | 5/1996 | Siczek et al. ................ | 378/197 |
| 5,717,732 A | * | 2/1998 | Tam ................................ | 378/4 |
| 6,200,024 B1 | * | 3/2001 | Negrelli ....................... | 378/197 |
| 6,431,751 B1 | * | 8/2002 | Everett et al. .............. | 378/197 |
| 6,640,123 B2 | * | 10/2003 | Warne et al. ............... | 600/407 |
| 6,735,280 B2 | | 5/2004 | Horbaschek | |
| 6,754,520 B2 | * | 6/2004 | DeSilets et al. ............ | 600/415 |
| 6,862,337 B2 | * | 3/2005 | Claus et al. .................. | 378/26 |
| 6,980,626 B2 | * | 12/2005 | Groh et al. .................... | 378/87 |
| 7,016,457 B1 | * | 3/2006 | Senzig et al. ................. | 378/19 |
| 2001/0036246 A1 | * | 11/2001 | Graumann .................... | 378/39 |
| 2002/0090058 A1 | * | 7/2002 | Yasuda et al. ............... | 378/205 |
| 2002/0118793 A1 | * | 8/2002 | Horbaschek ................. | 378/197 |
| 2003/0063703 A1 | * | 4/2003 | Moore .......................... | 378/17 |
| 2003/0091156 A1 | * | 5/2003 | Crain et al. .................. | 378/197 |
| 2003/0112926 A1 | * | 6/2003 | Atzinger ...................... | 378/196 |
| 2003/0202637 A1 | * | 10/2003 | Yang ............................ | 378/210 |
| 2004/0125918 A1 | * | 7/2004 | Shanmugavel et al. .... | 378/98.8 |
| 2004/0202285 A1 | * | 10/2004 | Masini ......................... | 378/197 |
| 2004/0234039 A1 | * | 11/2004 | Karaus et al. ............... | 378/196 |
| 2005/0265523 A1 | * | 12/2005 | Strobel ......................... | 378/193 |
| 2006/0029181 A1 | * | 2/2006 | Chen et al. ................... | 378/17 |
| 2006/0039537 A1 | * | 2/2006 | Strobel ......................... | 378/197 |

FOREIGN PATENT DOCUMENTS

DE    101 33 657 A1   1/2003
EP    0 098 398 A2    1/1984

* cited by examiner

*Primary Examiner*—Edward J. Glick
*Assistant Examiner*—Anastasia S. Midkiff

(57) ABSTRACT

An x-ray device for recording projection images of a patient features a C-arm on the ends of which an x-ray source and an x-ray detector are accommodated. The x-ray detector is accommodated on the C-arm so that translation movements can be executed with the x-ray detector in relation to the C-arm. This allows the angulation area or the area of the x-ray device with which an image can be recorded to be increased.

7 Claims, 4 Drawing Sheets

DEVICE FOR RECORDING PROJECTION IMAGES

CROSS REFERENCE TO RELATED APPLICATIONS

This application claims priority to the German Application No. 10 2005 014 188.9, filed Mar. 29, 2005 which is incorporated by reference herein in its entirety.

FIELD OF INVENTION

The invention relates to a device for recording projection images with:
- A radiation source mounted on a support and movable around the object and
- A radiation detector mounted on the opposite side of the support from the object and movable around the object in accordance with the movement of the radiation source, which receives radiation emitted by the radiation source and creates projection images of the object from this.

BACKGROUND OF INVENTION

This type of device is known from DE 101 33 657 A1. The known device features a C-arm which can be rotated around the object, which features a radiation source at one end and a radiation detector at the other. To enable the radiation detector to be moved as close as possible to the object to be investigated, the radiation detector is supported so that it can rotated on the C-arm. As a result of the ability to rotate the radiation detector into any position relative to the C arm, the radiation detector can be aligned so that, despite that fact that it is as close as possible to the object to be examined, for example a patient, a patient table or such like, it does not collide with it. Thus the radiation detector of the known device does not have to be exchanged in particular applications. Instead it is possible to adapt the device to the relevant application by rotating the radiation detector.

SUMMARY OF INVENTION

A disadvantage of the known device is that a radiation detector with a rectangular-shaped detector surface can only be rotated if it is in a position which allows the radiation detector to be rotated without colliding with anything. If the distance is too small the corners of the radiation detector collide with the obstacle. However there is the opportunity of basically rotating the radiation detector before it approaches an obstacle so that it can be moves as close as possible to the obstacle. The other option is to first move the radiation detector back if it is established that it is necessary to rotate the radiation detector. After the radiation detector is rotated it is moved towards the obstacle again. However in practice both these methods are rather cumbersome.

An object of the invention is thus to create a device for recording projection images which allows obstacles to be negotiated in a flexible manner.

This object is achieved by a device with the features of the independent claim. Advantageous embodiments and developments are specified in their dependent claims.

The outstanding feature of the device is that a translation movement can be performed with the radiation detector opposite the support. The option of performing a translation movement in relation to the support enables the radiation detector to be moved into the immediate vicinity of an obstacle in such a way that the movement of the support can be continued without interruption. In particular it is not necessary to first move the support with the radiation detector back in order to bring the radiation detector into the appropriate position and subsequently move the support with the radiation detector up to the obstacle again. In addition the device provides a large degree of flexibility since the radiation detector, on approaching an obstacle, does not have to be moved into the appropriate position in advance.

In a preferred embodiment is the radiation detector can be moved relative to the support while remaining at the same distance from it. This is sufficient if the support is in a position in which the spacing between the radiation detector and the object does not change with this type of movement.

In a further preferred embodiment the radiation detector is a position to perform the translation movement with a simultaneous change to the distance between the support and the radiation detector. This facility ensures that the distance between the radiation detector and the object to be investigated can remain largely the same in each case.

Furthermore provision can be made for the radiation source to be able to perform one of the translation movements which follows the translation movement of the radiation detector. In this way the imaging geometry can be largely retained if the radiation detector is moved.

Furthermore a monitoring device can be provided which is used to monitor the movement of the radiation detector and the radiation source for possible collisions. If there is a danger of a collision, the monitoring device initiates a translation movement of the radiation detector and if necessary of the radiation source through which the collision is avoided.

BRIEF DESCRIPTION OF THE DRAWINGS

Further details and advantages of the device can be taken from the description below, in which the exemplary embodiments of the invention are explained in detail on the basis of the enclosed drawing. The figures show.

DETAILED DESCRIPTION OF INVENTION

Figure 1:
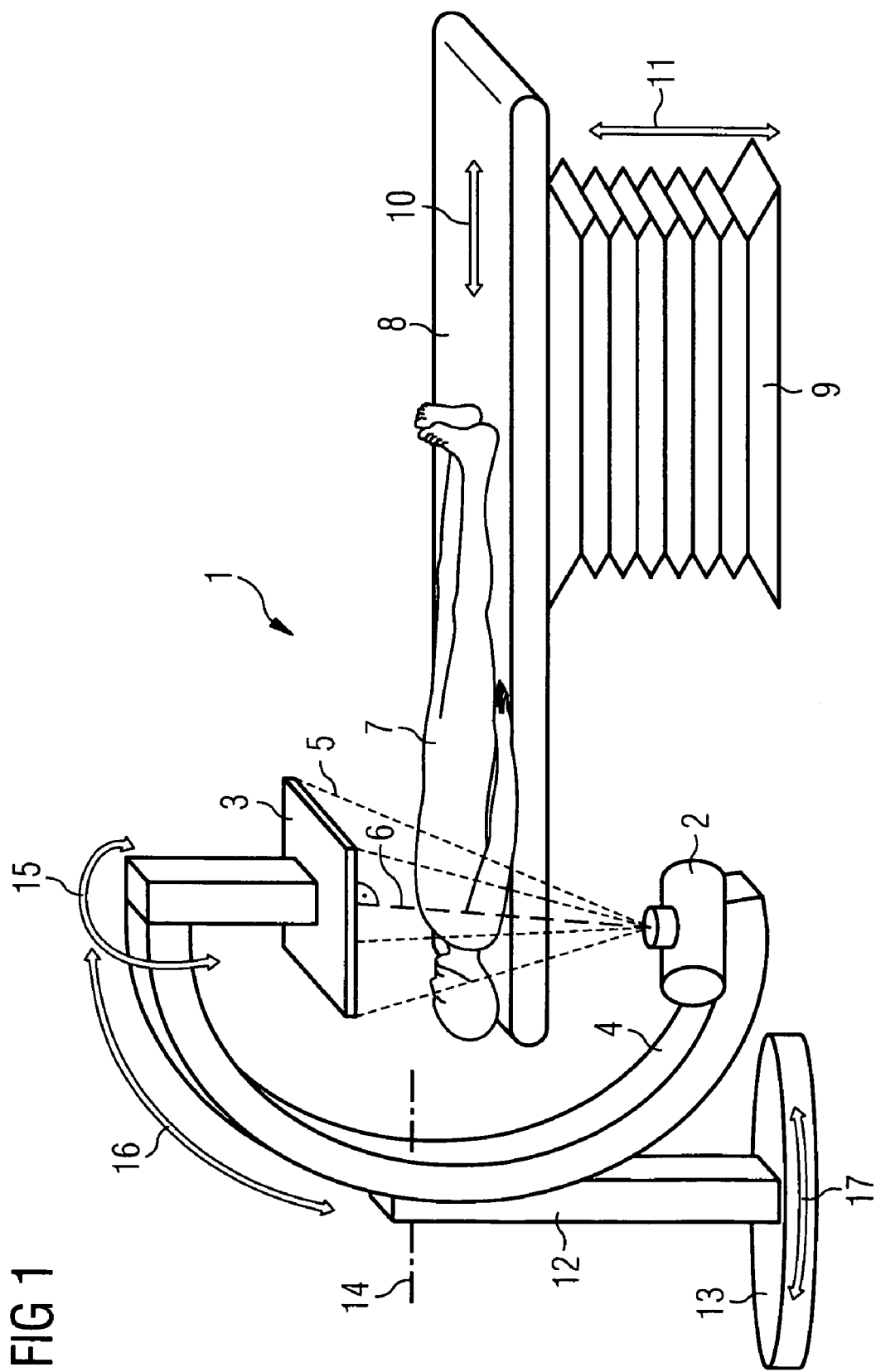
FIG. 1 a side view of the x-ray device with a C-arm.

FIG. 1 shows an x-ray device 1 with an x-ray source 2 and an x-ray detector 3. The x-ray source 2 and the x-ray detector 3 are each accommodated on the ends of a C-arm 4.

The x-ray source 2 sends x-ray radiation 5 indicated by dashed lines in FIG. 1 to the x-ray detector 3. An x-ray hitting the x-ray detector 3 at a right angle is designated in this case as the central ray 6. The x-ray radiation 5 passes through a patient 7 located on a patient bed 8. The patient bed 8 is mounted on a support 9 with bearings in the support enabling the patient bed to be moved in a lengthwise direction 10 and in an up-and-down direction 11. In addition the patient bed 8 can also move on bearings so that the patient bed 8 can be rotated around a vertical axis.

The C-arm 4 is mounted via a support 12 on a pedestal 13. The C-arm 4 mounted on the support 12 can on the one hand be rotated around a pivot axis 14. In this case the C-arm 4 performs a pivot movement 15. Furthermore the C-arm 4 can execute a tilting movement 16, whereby the C-arm 4 is moved in a circumferential direction in a bearing mounted on the support 12 not shown in FIG. 1. Finally the bearing for the pedestal 13 also allows a rotational movement 17 around a vertical axis. It is further possible for the pedestal 13 to be able to be moved on rails. In this manner for example the support 12 can be moved into a position next to the patient bed 8.

Figure 2:
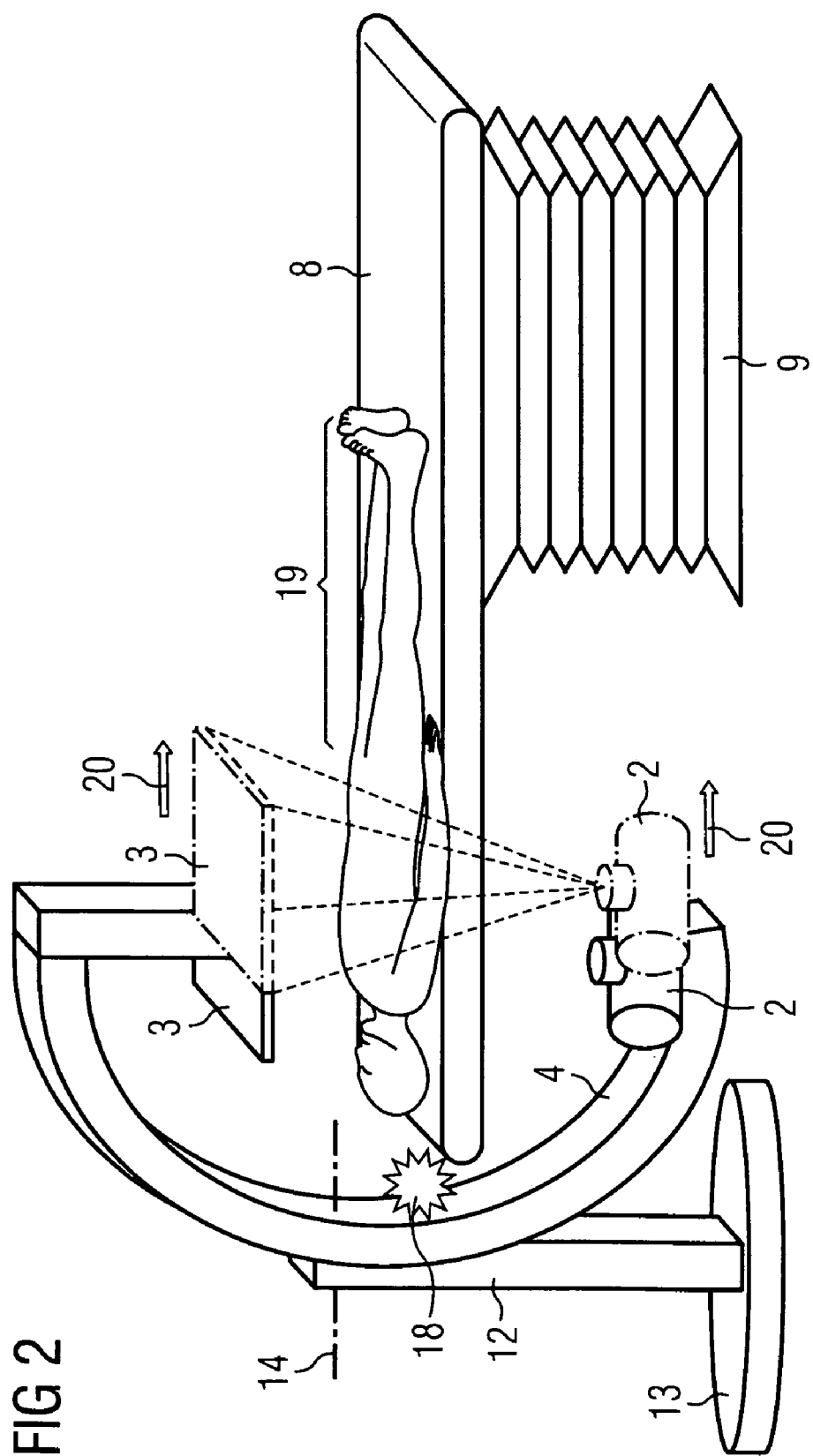
FIG. 2 a side view of the x-ray device from FIG. 1, of which the x-ray detector and its x-ray source have executed a sideways translation movement.

Despite the many possibilities for positioning the x-ray source 2 and the x-ray detector 3 as well as the patient 7, situations can occur in which, as shown in FIG. 2, there is a danger of a collision 18 between the patient bed 8 and the C-arm 4. These types of collisions occur especially with biplanar x-ray devices with two C-arms or where space constraints come into play. These types of space constraints arise especially when the x-ray device 1 is combined with a system for magnetic navigation. In this case 8 magnetic pole shoes are located alongside the patient bed 8 which restrict the options for moving the C-arm 4 out of the way. Imaging of caudal regions of the body 19 cannot then be undertaken.

If the C-arm 4, as shown in FIG. 2 is in an anterior-posterior orientation, a forwards movement 20 of x-ray source 2 and x-ray detector 3 allows imaging of at least part of the caudal body region 19. The imaging geometry does not change in this case through the forwards movement 20 of x-ray source 2 and x-ray detector 3. It should be pointed out that with an anterior-posterior orientation of the C-arm 4 of the central ray 6 assumes a right angle to the longitudinal axis of the patient bed 8.

Figure 3:
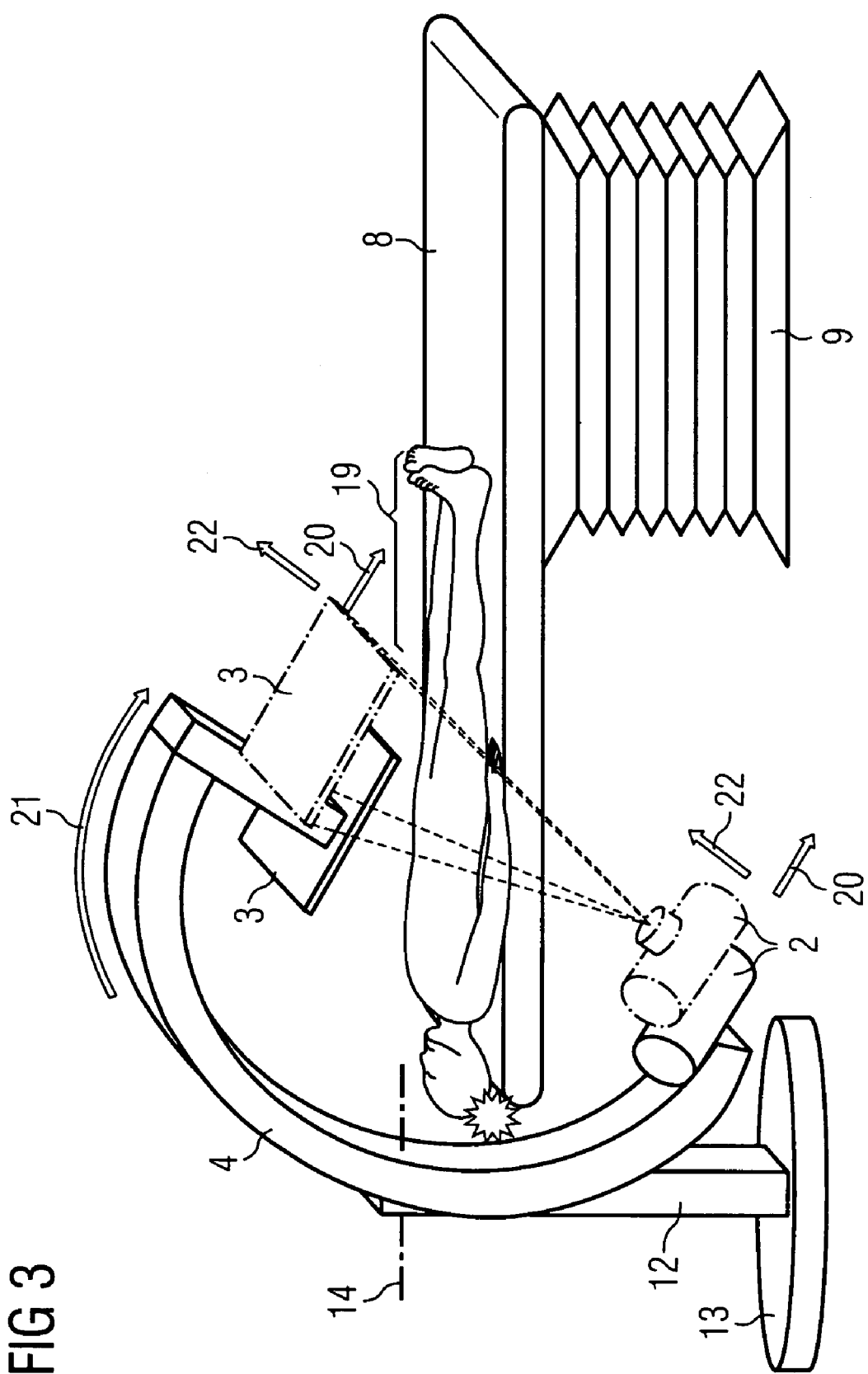
FIG. 3 a side view of the x-ray device from FIG. 1 with tilted C-arm, of which the x-ray source and x-ray detector have performed a translation movement in two directions.

In FIG. 3 the C-arm 4 is angled for caudal imaging by a tilting movement 21. If the x-ray source 2 and the x-ray detector 3 are now moved in accordance with the forwards movement 20 in FIG. 2 so that the distance between the end of the C-arm 4 and the x-ray detector 3 or the x-ray source 2 remains unchanged, with this type of forwards movement the distances between the x-ray source 2 and the area of the patient's body 7 to be examined as well as between the area of the patient's body to be examined and the x-ray detector change. As a consequence the imaging geometry would change. The imaging geometry can however be largely preserved by the x-ray source 2 and the x-ray detector 3 not only executing the forwards movement 20 but also a lifting movement 22. By executing the forwards movement 20 and the lifting movement 22 the imaging geometry remains unchanged and the size of the area for which an image can be recorded can be increased.

With a right-anterior-oblique or a left-anterior-oblique setting of the C-arm 4 it can be necessary for the x-ray source 2 and the x-ray detector 3 to be able to execute a sideways movement to the left or to the right. The left or right directional specifications relate in this case to the sideways directions, if the C-arm 4 is located in the anterior-posterior position and the observer is looking in the direction of the pivot axis 14 towards the ends of the C-arm 4.

Preferably the x-ray source 2 and the x-ray detector 3 are thus able to be moved with three degrees of freedom. In the anterior-posterior position these are the translation movements to the right and left, upwards and downwards and also backwards and forwards.

Figure 4:
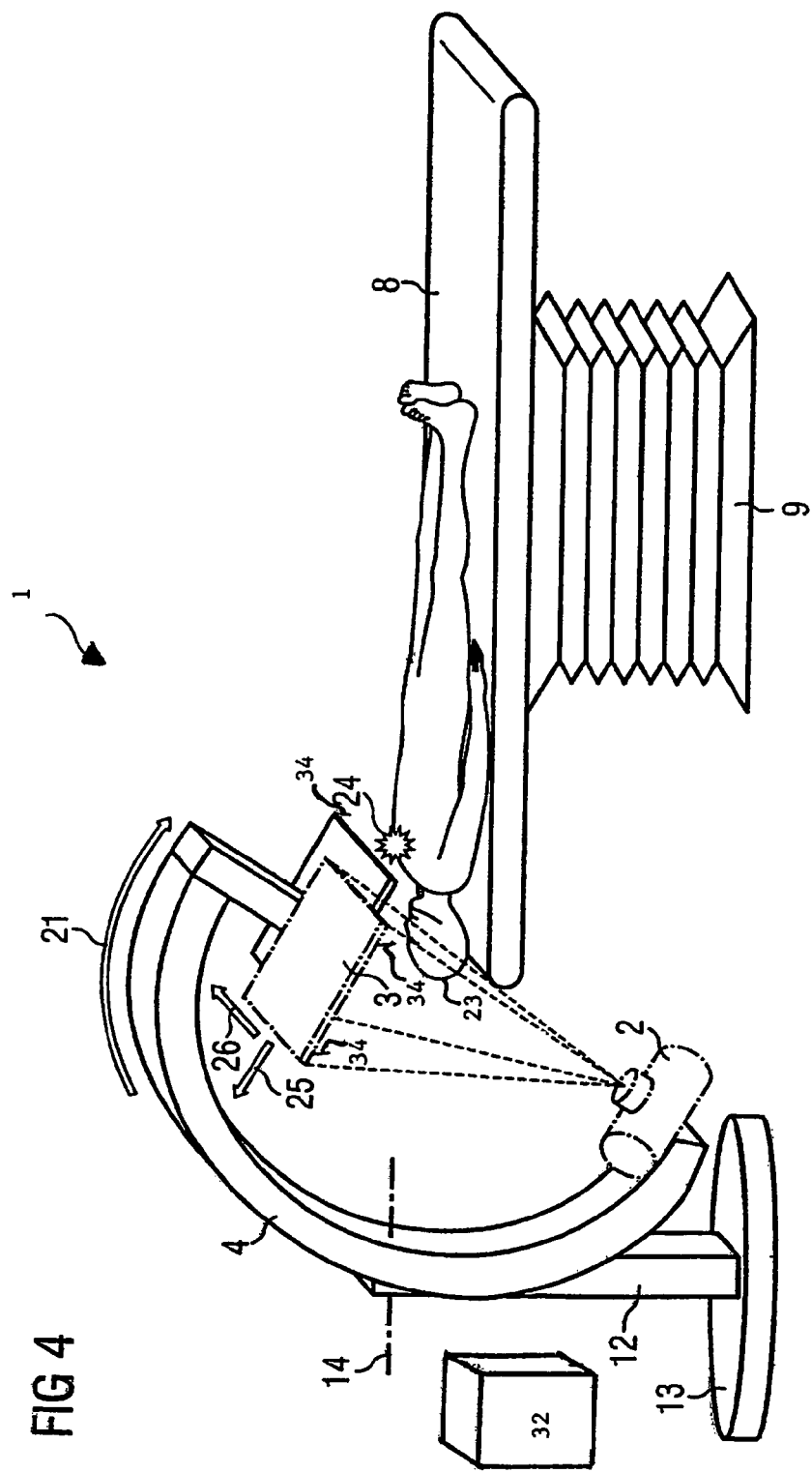
FIG. 4 a side view of the x-ray device from FIG. 1 with tilted C-arm, in which only x-ray detector has performed a translation movement.

FIG. 4 finally shows a special case which frequently occurs for x-ray images recorded in the area of a skull 23 of the patient 7. The hallmark of this situation is that the physician needs a specific angulation of the C-arm 4 to record an image of a specific anatomical structure. It is not possible to do without this angulation. When extended surface area x-ray detectors 3 are used however the necessary angulation cannot be achieved, since this would lead to a collision 24 with the body of the patient 7. A backwards movement 25 in combination with a lifting movement 26 however makes the desired angulation possible. In this case the user does not obtain any additional surface for recording an image, such as described in conjunction with FIGS. 2 and 3, but rather a larger angulation area. The option of moving the x-ray detector 3 enables the large-area x-ray detectors 3 which are preferred per se to be used in this case.

With the exemplary embodiment shown in FIG. 4 the physician loses imaging surface. This is no disadvantage however, since the lost detector surface is not needed for illumination of the skull 23.

To avoid imposing an unnecessary radiation strain on the patient 7 and to exploit the complete shifted surface of the x-ray detector 3, the display of the collimator in the area of the x-ray source 2 can be adapted. With a modified exemplary embodiment the x-ray source 2 can also be shifted.

The exemplary embodiments described here provide a series of advantages. On the one hand the area over which an image can be recorded is increased when there is a danger of a collision of the C-arm 4 with the patient bed 8. On the other hand the angulation area is increased when large-area x-ray detectors are used. The x-ray device 1 thus has the advantages that are produced in each case when using x-ray detectors 3 with a larger and smaller imaging surface.

It should be pointed out that exemplary embodiments described here each include a C-arm 4. In accordance with the exemplary embodiments described here biplanar x-ray devices, which feature at least two C-arms 4 each with an x-ray source 2 and an x-ray detector 3, can be modified accordingly.

It should also be mentioned that the forwards movement 20, the lifting movement 22 as well as the backwards movement 25 can be initiated by a monitoring device in each case which identifies the danger of a collision and controls the movement of the x-ray source 2 and of the x-ray detector 3 suitably. The monitoring device can for example be a computer system that contains in a memory unit the allowed range of values for the position parameters. If the limits of the allowed parameter values are approached the translation movement is then initiated. In addition it is possible to equip the edges of the x-ray detector 3 with sensors with the aid of which the monitoring device can identify when an obstacle is being approached.

The invention claimed is:

1. A device for recording projection images, comprising:
   a C-arm support;
   a radiation source arranged on the support and configured to be moved with the support to be positionable about a patient placed on a patient bed so that the radiation passes through the patient;
   a radiation detector arranged on an opposite side of the support relative to the radiation source and configured to be moved around the patient in accordance with movement of the radiation source;
   said apparatus having an imaging geometry in which the radiation source and the radiation detector face each other;

said radiation detector further configured to detect radiation emitted by the radiation source and to generate projection images of the patient based on the detected radiation; and, a controller configured to:
  move, by a moving device, the radiation detector;
    (i) translatorily relative to the support; and,
    (ii) translatorily relative to the source;
  wherein the translatory movements of the radiation detector include parallel movements relative to a center radiation beam emitted by the radiation source;
  execute both a forward movement of the radiation detector relative to a lengthwise direction along the patient bed and a lifting movement of the radiation detector relative to the lengthwise direction along the patient bed; and,
  wherein, during said movements, said imaging geometry is preserved and the size of the area for which the image is to be recorded is increased, while said C-arm support is angled for caudal imaging with a tilting movement by a tilting device.

2. The device in accordance with claim 1, wherein the translatory movements of the radiation detector includes an orthogonal movement relative to a center radiation beam emitted by the radiation source.

3. The device in accordance with claim 1, wherein the radiation source is configured to be moved translatorily corresponding to and following the translatory movement of the radiation detector.

4. The device in accordance with claim 1, further comprising:
  a monitoring device for detecting a danger of collision by the radiation source or by the radiation detector while operating the device and for controlling the translatory movement by the radiation source or by the radiation detector to avoid the collision.

5. The device in accordance with claim 1, wherein the support is a curved arm configured to be moved in a circumferential direction and to be pivoted round a radial axis of rotation.

6. The device in accordance with claim 1, further comprising only one x-ray source and only one x-ray detector.

7. A device for recording projection images, comprising:
a radiation source arranged on a C-arm support and configured to be moved with the support around an imaging object;

a radiation detector arranged on an opposite side of the support relative to the radiation source and configured to be moved around the imaging object in accordance with the moving of the radiation source, the radiation detector further configured to detect radiation emitted by the radiation source and to generate projection images of the imaging object based on the detected radiation;

said apparatus having an imaging geometry in which the radiation source and the radiation detector face each other;

a controller configured to:
  move, by a moving device, the radiation detector;
    (i) translatorily relative to the support; and,
    (ii) translatorily relative to the source;
  wherein the translatory movements of the radiation detector include parallel movements relative to a center radiation beam emitted by the radiation source;
  execute both a forward movement of the radiation detector relative to a lengthwise direction along the patient bed and a lifting movement of the radiation detector relative to the lengthwise direction along the patient; and
  wherein, during said movements, said imaging geometry is preserved and the size of the area for which the image is to be recorded is increased, while said C-arm support is angled for caudal imaging with a tilting movement by a tilting device; and, a monitoring device for detecting a danger of collision by the radiation source or by the radiation detector while operating the device and for controlling the translatory movement by the radiation source or by of the radiation detector to avoid the collision.

* * * * *